United States Patent [19]
Conche

[11] Patent Number: 5,309,774
[45] Date of Patent: May 10, 1994

[54] INSTALLATION FOR TAKING FLUID SAMPLES IN A CONFINED AREA

[75] Inventor: François Conche, Cherbourg, France

[73] Assignee: Cogema-Compagnie Generale Des Matieres Nucleaires, France

[21] Appl. No.: 870,835

[22] Filed: Apr. 20, 1992

[30] Foreign Application Priority Data

Apr. 23, 1991 [FR] France ............... 91 04995

[51] Int. Cl.⁵ .................. G01N 1/10; G01N 1/14
[52] U.S. Cl. ................. 73/863.32; 73/864.31; 73/864.23; 73/863.81
[58] Field of Search .......... 73/863.32, 864.31, 864.23, 73/863.81, 863.85, 863.86, 863.82, 863.01, 864.51, 864.52, 864, 864.24, 864.25, 864.33

[56] References Cited

U.S. PATENT DOCUMENTS

| | | | |
|---|---|---|---|
| 2,968,183 | 1/1961 | Hannaford et al. | 73/864.31 X |
| 3,026,730 | 3/1962 | Howarth et al. | 73/864.52 |
| 3,192,968 | 7/1965 | Baruch et al. | 73/864.24 X |
| 3,418,080 | 12/1968 | Rochte et al. | 73/864.23 X |
| 4,493,792 | 1/1985 | Graf, Jr. | 976/DIG. 374 X |
| 4,512,203 | 4/1985 | Calame-Longjean et al. | 73/863.81 |
| 4,516,436 | 5/1985 | Conche et al. | 73/863.85 |
| 4,577,112 | 3/1986 | Conche et al. | 976/DIG. 343 X |
| 4,662,231 | 5/1987 | Schaarschmidt et al. | 73/864.23 X |
| 4,665,758 | 5/1987 | Schaarschmidt | 73/863.32 |
| 4,854,355 | 8/1989 | Chazot et al. | 73/863.01 X |

FOREIGN PATENT DOCUMENTS

| | | |
|---|---|---|
| 78211 | 5/1983 | European Pat. Off. |
| 296917 | 12/1988 | European Pat. Off. |
| 1287828 | 1/1969 | Fed. Rep. of Germany ... 73/863.81 |
| 2515350 | 4/1983 | France |
| 2516242 | 5/1983 | France |
| 2203243 | 10/1988 | United Kingdom |

*Primary Examiner*—Tom Noland
*Attorney, Agent, or Firm*—Pearne, Gordon, McCoy & Granger

[57] ABSTRACT

For taking liquid samples, such as active solutions in an irradiated nuclear fuel processing plant within a confined area (10) located below a protective slab (12), use is made of vacuum pots (44), which are pneumatically transferred into a vessel (14) located beneath the slab and which are engaged on needles (40) supplied with fluid to be sampled and projecting into the bottom of the vessel. A pot (44) is moved pneumatically into a nacelle, pod or basket (76) of a rotary drum (72) by means of a transfer duct (60), which passes through a slab element (62) installed in a rotary plug (20). The positioning of the pot vertically with respect to a needle (40) is ensured by the combined rotations of the drum (72) and the plug (20). A vertical displacement of the slab element (62) ensures the sampling before the filled pot is pneumatically evacuated by the reverse path.

15 Claims, 9 Drawing Sheets

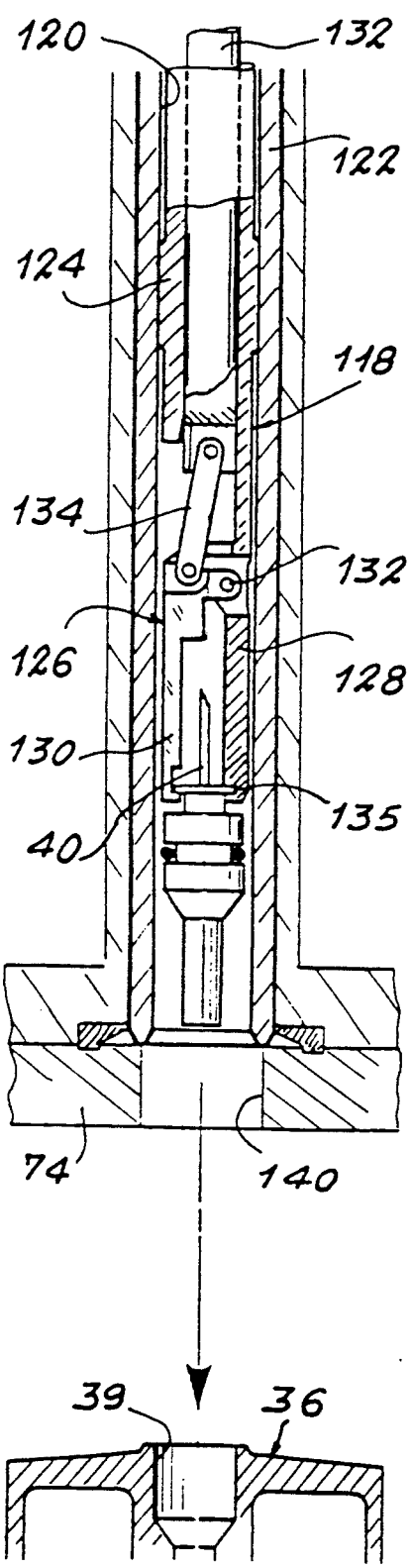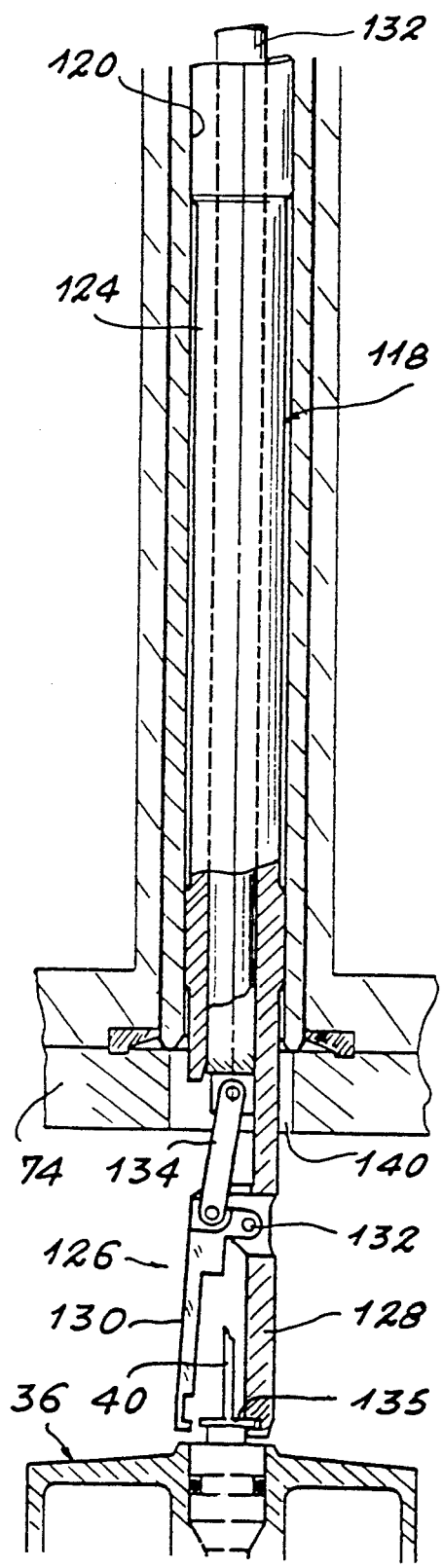
FIG. 8 A
FIG. 8 B

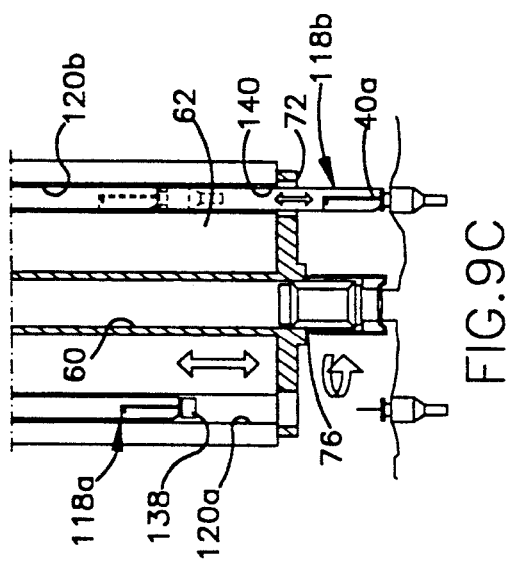
FIG.9C
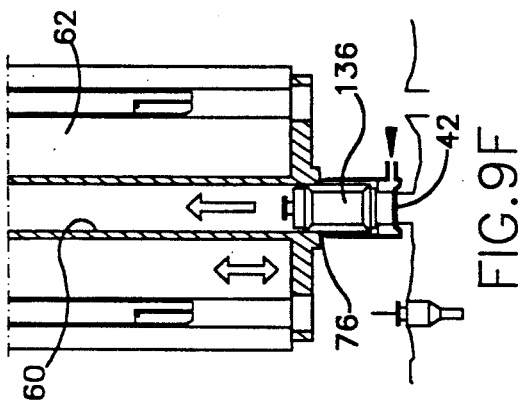
FIG.9F
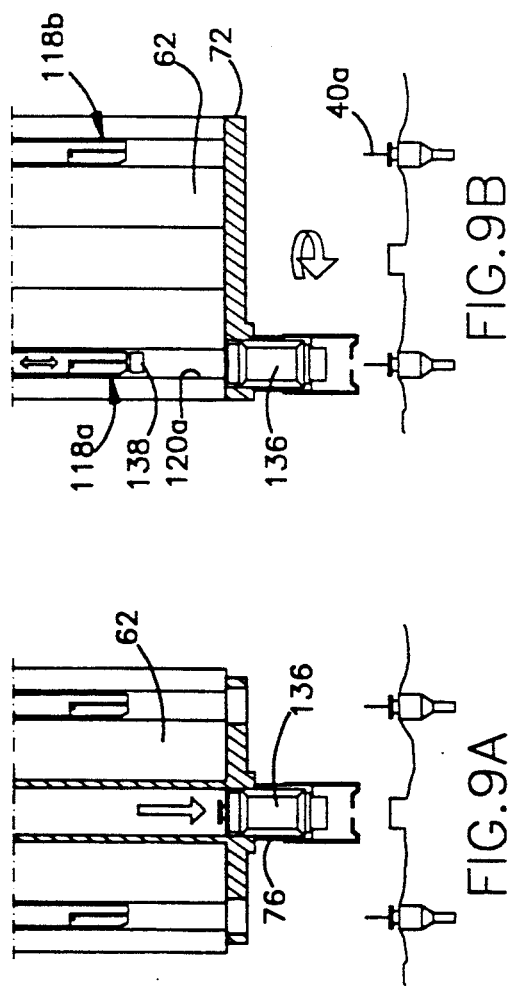
FIG.9B
FIG.9E
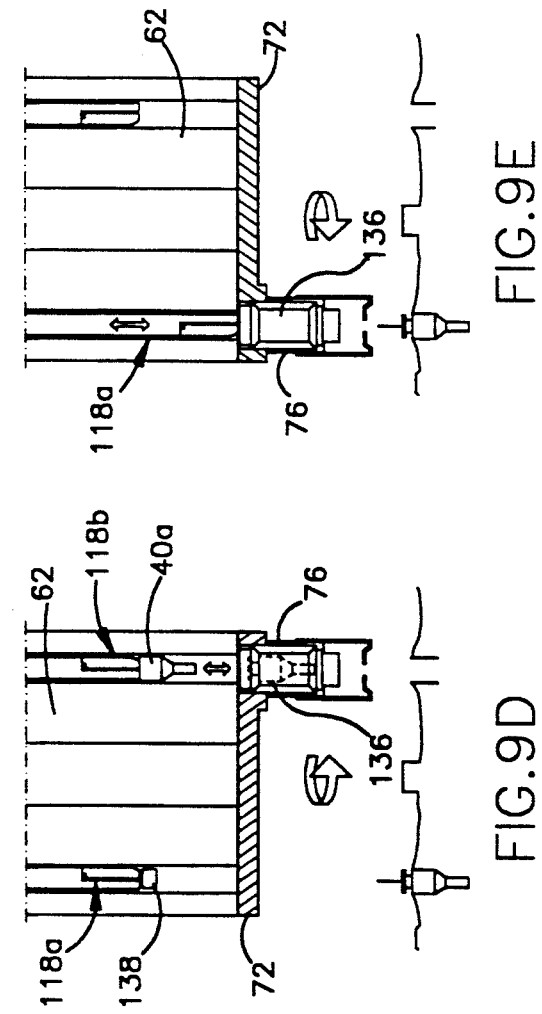
FIG.9A
FIG.9D

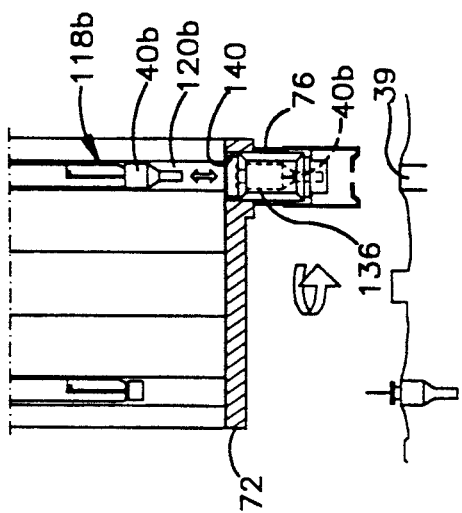
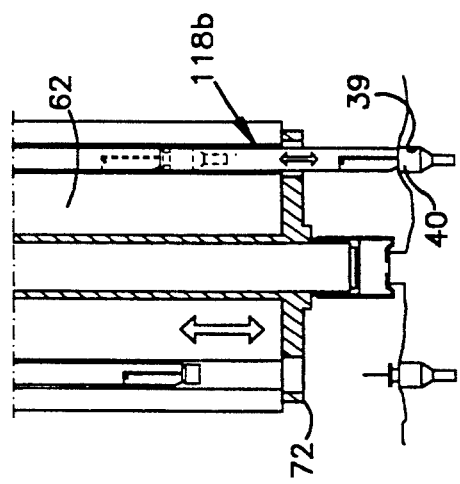
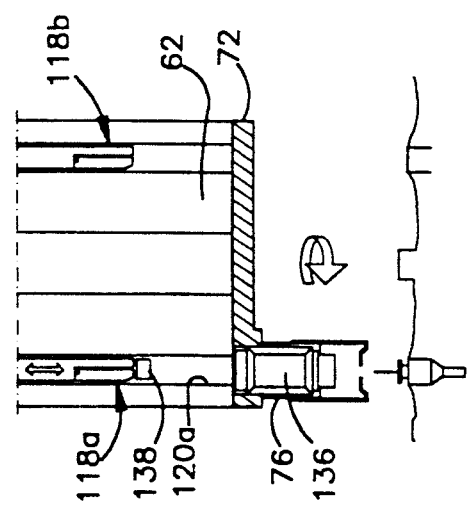
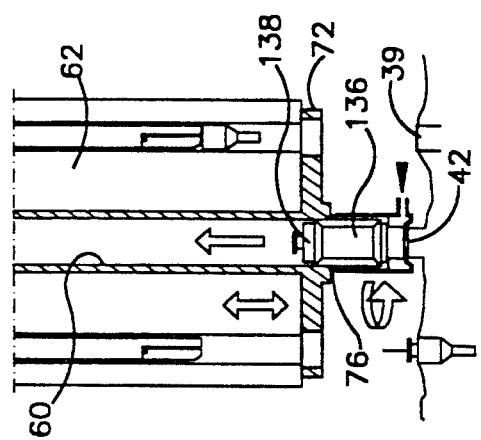
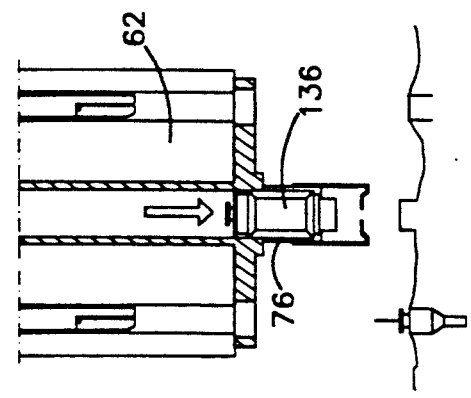
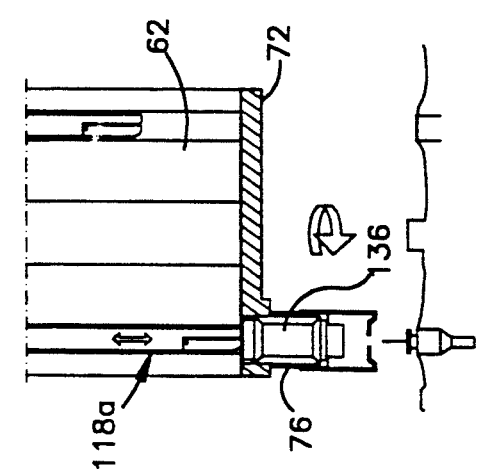

INSTALLATION FOR TAKING FLUID SAMPLES IN A CONFINED AREA

BACKGROUND OF THE INVENTION

1. Field of the Invention

The invention relates to an installation designed for remotely carrying out the taking of fluid samples, such as radioactive liquids within a confined area positioned below a biological protection slab.

2. Description of the Related Art

Several installations of this type can be placed in an irradiated nuclear fuel processing plant in order to carry out in an automated, remote manner the taking of samples of active solutions in different parts of the plant. They make it possible to introduce in a controlled manner fluid samples into containers known as pots, which are made from flexible plastic materials and which have been previously placed under a vacuum, prior to analyzing the said samples in the laboratory.

In order to ensure an optimum biological protection of personnel against α particles and γ rays, without having to give to the equipment used an excessive weight and volume, FR-A-2 515 350 proposes carrying out the sampling operations directly within a vessel positioned below the biological protection slab. For this purpose the pots pass through the slab before being engaged on needles located in the bottom of the vessel and towards which are moved various fluids to be subject to the sampling operations. To this end, each of the needles passes, below the bottom of the slab, into a container supplied with fluid by a circuit, such as that described in FR-A-2 516 242.

In such an installation, the main problem is the transfer of the pots through the slab, as well as the actual sampling operation, which must be carried out blind and in an automated manner.

The solution to these problems described in FR-A-2 515 350 is completely mechanical. Thus, when introduced into the installation by a pneumatic transfer system, the pot is moved by a horizontal piston up to the upper end of a well in which its descent is controlled by the rotation of a vertical endless screw traversing the slab. In the bottom of the well, the pot is taken up by a vertically axed rotary barrel, where a rotation thereof has the effect of bringing the pot below a gripping tool traversing the said slab. This gripping tool controls the descent of the pot and ensures the sampling by engaging the pot on the needle. In order to have access to several needles arranged along one or more circular arcs in the vessel bottom, said assembly is installed on a rotary plug belonging to the slab and whose axis coincides with that of said circular arcs.

Such a mechanism is relatively complex and suffers from unacceptable risks with regards to the jamming of the pots, particularly when the latter are moved by the piston and during their descent into the well controlled by the endless screw. It is clear that the jamming of a pot when traversing the slab would involve a particularly difficult and dangerous intervention on behalf of the personnel.

Moreover, the installation described in the aforementioned document involves, when sampling has taken place, a discharge of the pots through the bottom of the vessel, which is compatible only with difficulty with the conventional arrangement of the laboratory for analyzing the samples taken outside the confined area. If it was considered that the filled pots should be evacuated by again passing them through the slab with the aid of the aforementioned mechanism, this would give rise to the use of various not described means, because the piston only permits pot transfer in one direction.

SUMMARY OF THE INVENTION

The invention relates to an installation for taking fluid samples using a sampling vessel positioned below the slab, but in which the remote handling of the pots making it possible to traverse the slab in both directions and for carrying out the sampling operation is ensured in a much more simple and reliable manner than in the prior art, so as to reduce to the greatest possible extent the risks of jamming of the pots and permitting without difficulty the evacuation of the filled pots to an analysis laboratory located outside the confined area.

According to the invention, this result is achieved by means of an installation for taking fluid samples in a confined area located below a protective slab, said installation comprising a sampling vessel located below the slab, at least one sampling needle traversing a bottom of the slab and remote handling means for transferring individually sampling pots into and out of the vessel through the slab and for engaging the pots individually on said sampling needle in order to perform a sampling operation, wherein said remote handling means comprise:

a pot transfer duct, traversing a slab element, which is vertically mobile between an upper waiting position and a lower sampling position;

a drum rotatably mounted beneath said slab element, about an axis displaced with respect to that of the duct, and having a pot reception nacelle which can be brought, by the rotation of the drum, into an angular pot reception and evacuation position, in which the nacelle is placed below the duct, and into at least one angular sampling position, in which the nacelle can be brought above the sampling needle; and means for the pneumatic transfer of the pots upwards and downwards in said duct.

In such a sampling installation, the pots under vacuum are directly transferred into the nacelle, basket or pod located below the slab by the pneumatic transfer system. A simple rotation of the drum brings the nacelle into a position in which sampling can be directly carried out by a descent of the slab element carrying the drum, without it being necessary to use any random gripping tool. Reverse movements of the slab element and the drum again bring the nacelle housing the filled pot vertically with respect to the transfer duct. The filled pot can then be moved by said duct to the analysis laboratory under the action of pneumatic transfer means.

As in the prior art, several sampling needles are advantageously placed in the bottom of the vessel, according to at least one circular arc whose axis is displaced with respect to that of the drum axis. A rotary plug, whose axis coincides with that of the arc, then forms above the vessel part of the slab and said slab element is housed in said rotary plug, so that in each angular sampling position of the nacelle, the latter can be brought above each of the needles by a rotation of the rotary plug.

The rotation of the drum can in particular be controlled by control means installed on said slab element and acting on a control shaft traversing the slab element along its axis and integral with the drum at its lower end.

The pneumatic pot transfer means can comprise an air supply pipe, which passes in said control shaft and issues below the nacelle. This pipe, which is normally linked with the vessel ventilation means via first means forming a valve is connected, when it is wished to evacuate or remote a filled pot, to compressed air supply means through the second means forming a valve.

In a preferred embodiment of the invention, each sampling needle is detachably fitted into a receptacle provided in the bottom of the vessel. Remote handling means then comprise an anti-tear out member fitted on the nacelle in such a way as to be able to move on the latter between a top position, in which said member is flush with the lower end of the nacelle, and a bottom position in which said member is spaced from the lower end of the nacelle by a distance substantially equal to the length of part of each needle projecting above the receptacle. Therefore the anti-tear out member continues to bear on the sampling needle, e.g. under the action of elastic means, during the raising of the pot due to its engagement on the needle and whilst the latter remains plunged in the pot, which avoids any risk of the needle being torn out at this moment.

In a preferred embodiment of the invention, the air supply pipe has a rigid tube, slidingly located in the control shaft and carrying the anti-tear off member at its lower end.

Preferably, to permit the replacement of a used needle and the putting into place of a new needle, the slab element has two cavities, whereof at least one can be supplied above a needle and under each of which can be brought the nacelle as a result of a rotation of the drum. A gripping tool is then slidingly located in each of the cavities, so as to be able to seize a pot plug or a needle.

Advantageously isolating or insulating means are placed above the slab and are connected to the transfer duct by a flexible tube. These insulating means can occupy an insulating position, in which the flexible tube is insulated from a transfer tube placed above the insulation means, and a passage position in which the flexible tube and the transfer tube are linked with one another.

The pneumatic pot transfer means can then comprise a second air supply pipe, which communicates with compressed air supply means through third means forming a valve and which issues into the transfer tube immediately above the insulating means.

In order to permit the automatic operation of the installation, various detectors are provided, such as a detector of the presence of a pot in the nacelle and a detector of the passage of a pot into the upper part of the transfer pipe, above the insulation means.

BRIEF DESCRIPTION OF THE DRAWINGS

The invention is described in greater detail hereinafter relative to a non-limitative embodiment and with reference to the attached drawings, which show:

FIGS. 8A to 8B Vertical sectional views illustrating the installation of a needle with the aid of a gripping tool incorporated into the sampling installation according to the invention.

FIGS. 9A to 9F Vertical sectional views diagrammatically illustrating different phases of the operation of the sampling installation according to the invention, during the removal of a used needle with the aid of the gripping tool of FIGS. 8A and 8B.

FIGS. 10A to 10F Vertical sectional views diagrammatically illustrating different phases of the operation of the sampling installation according to the invention during the fitting of a new needle.

DETAILED DESCRIPTION OF THE PREFERRED EMBODIMENTS

Figure 1:
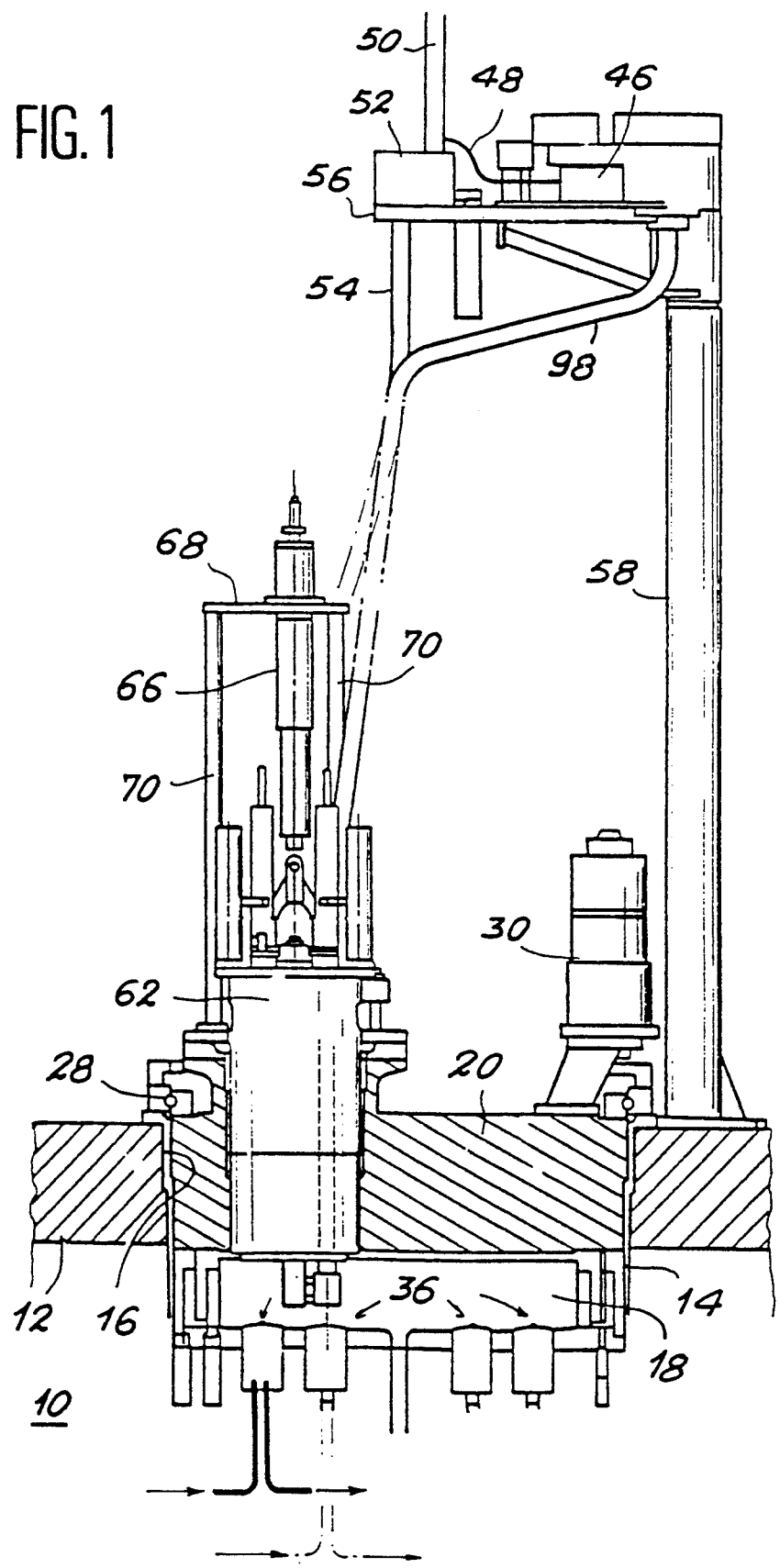
FIG. 1 A side view in partial section diagrammatically showing an installation for taking fluid samples according to the invention.

The installation shown in the drawings is designed for automatically and remotely removing active solution samples in a confined area 10 upwardly defined by a horizontal, biological protection slab 12. In an exemplified manner, the confined area 10 can house a single irradiated nuclear fuel chemical treatment unit.

Figure 2:
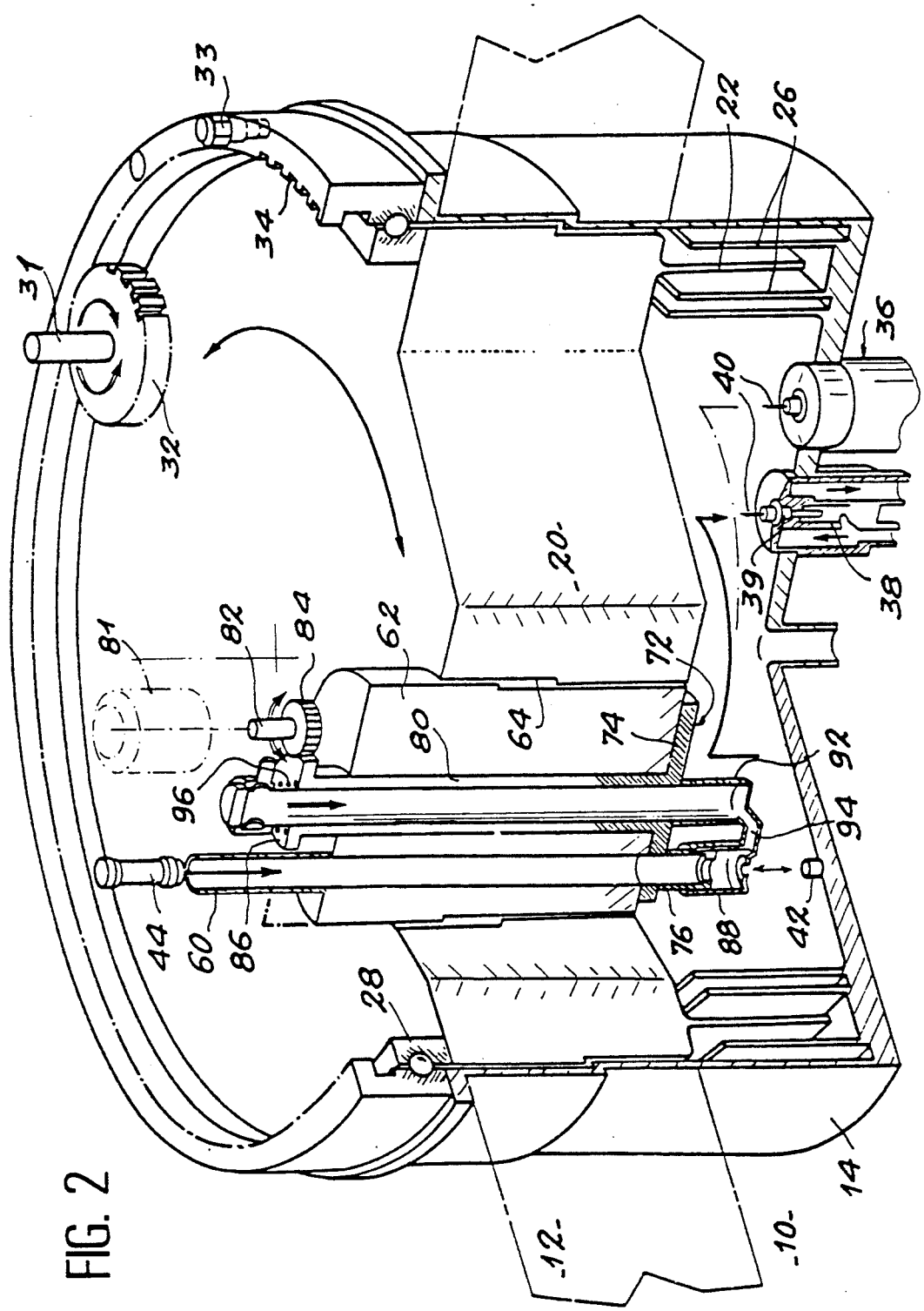
FIG. 2 A perspective view illustrating on a larger scale that part of the installation positioned level with the slab and below the latter.

As can be seen in FIGS. 1 and 2, the sampling installation according to the invention comprises a vertically axed, cylindrical vessel 14 placed in a circular opening 16 formed in the slab 12 and suspended on the latter, so as to define within the confined area 10 a closed volume 18 closed in its upper part by a rotary plug 20 forming part of the biological protection slab 12.

The seal between the rotary plug 20 and the vessel 14 is ensured by a hydraulic joint formed between a cylindrical wall 22, which projects downwards on the periphery of the plug 20 and a hydraulic guard in which is embedded the cylindrical wall 22 and which is formed between two double cylindrical walls 24, which project upwards on either side of the wall 22, on the periphery of the substantially planar, horizontal bottom of the vessel 14.

The rotary plug 20 is supported in rotary manner in the vessel 14, e.g. by a ball bearing 28. The control of the rotation of the plug 20 is ensured by a geared motor means 30 (FIG. 1) installed on the upper face of the plug and whose vertical output shaft 31 drives a driving pinion 32 (FIG. 2), which engages on a toothed ring 34 installed on an upper flange of the vessel 14.

To ensure a precise angular positioning of the rotary plug 20, the geared motor means 30 has a direct current gear changer and a tachogenerator. Moreover, the angular positioning is known by means of a coder, a bolt 33 being operated whenever the rotary plug reaches a predetermined angular position corresponding to the taking of a sample. The correct operation of this plug, constituted by a pin operated by a direct current motor, is controlled by a position sensor and by a linear displacement sensor or transducer.

As is more particularly illustrated by FIGS. 1 and 2, the bottom of the vessel 14 has sampling heads 36 mainly constituted by a sampling container 38 integral with the vessel bottom and a sampling needle 40, whose body is detachably fitted into a receptacle 39 of the sampling container from the interior of the vessel 14.

Each of the sampling containers 38 is connected by a circuit, which does not form part of the invention, to a given part of the chemical unit located within the confined area 10, in such a way that different fluids, or identical fluids sampled at different locations, circulate in each of the sampling containers 38. The fitting of the needles 40 in said containers 38 is such that the lower part of each of the needles is immersed in the corresponding fluid.

Figure 4:
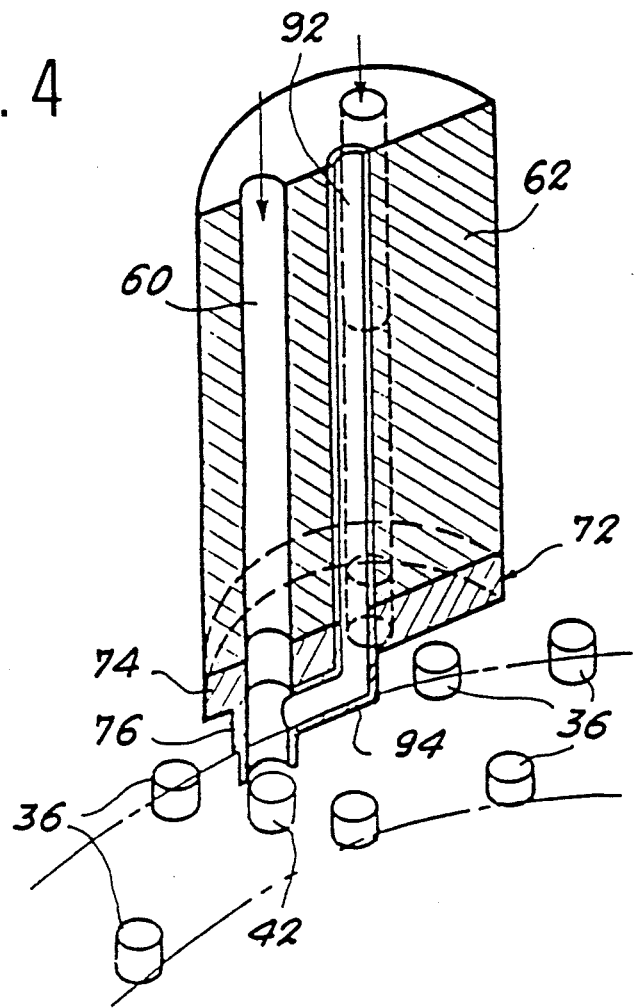
FIG. 4 A perspective, part vertical sectional view diagrammatically illustrating the position of the slab element for the passage of the pot with respect to the arrangement of the needles in the bottom of the vessel.
Figure 5:
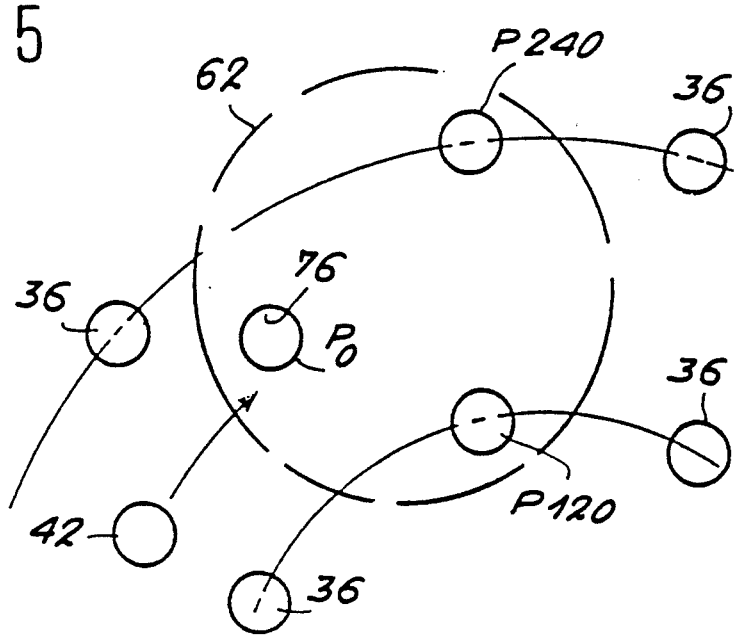
FIG. 5 A plan view diagrammatically illustrating the positions which can be occupied by the pot transfer pipe with respect to the needles installed in the vessel bottom.

As is more particularly illustrated by FIGS. 2, 4 and 5, the sampling heads 36 are located in the bottom of the vessel 14 along two concentric circular arcs, whose axis coincides with the vertical axis of the vessel 14 and the rotary plug 20.

In the bottom of the vessel 14 there is also a confinement member 42 in the form of a vertically axed cylindrical pin, which is equidistant of the two circular arcs on which are arranged the sampling heads 36. A second confinement member 42, which is symmetrical with respect to the first relative to the vertical axis of the vessel, is advantageously provided for replacing the first one, should the latter become damaged.

The sampling installation according to the invention is designed for taking fluid samples in pots 44, made from a flexible plastics material and previously placed under a vacuum, by the engagement of these pots on one or other of the needles 40.

In practice, the pots 44 are generally constituted by an external envelope, referred to as a cursor, whose shape is designed so as to permit the pneumatic transfer of the pots in tubes without any risk of jamming, as well as the actual pot, placed within said envelope and having at its downwardly turned end when it enters the installation a plug which can be perforated by the needles 40 during sampling operations. Essentially this arrangement is comparable to that described in FR-A-8 120 039, so that reference should be made thereto for a more detailed description.

As a variant, it should be noted that the pots 44 can be made in one piece, the actual pot then having the external shape of the cursor in the preceding case.

The vacuum pots for carrying out the fluid sampling operations are individually passed when requested to the sampling installation according to the invention from a not shown distribution station, which does not form part of the invention. It should be noted that each of the vacuum pots is advantageously identified by a marking prior to its dispatch, so that each pot 44 can then be distinguished from the others during sampling and during the analyses carried out on the samples taken.

Figure 6:
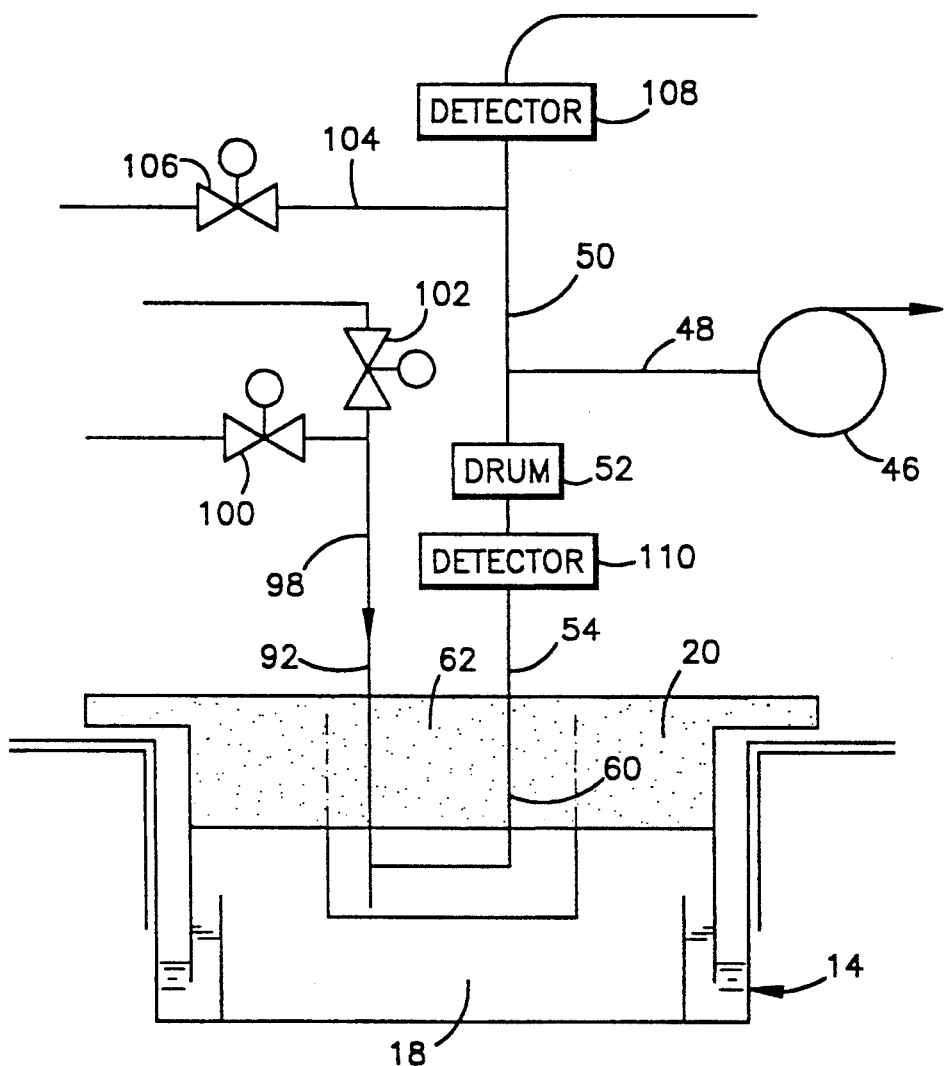
FIG. 6 A diagram showing the pneumatic pot transfer circuit in the installation.

The transfer of each vacuum pot between the distribution station and the sampling installation according to the invention takes place pneumatically, the pot travelling in a tube by suction, under the action of a suction station represented in FIGS. 1 and 6 by a pump 46 and located at the entrance of the sampling installation according to the invention.

More specifically, the pump 46 is located on a pipe 48 branched immediately above a pneumatic drum 52 on a transfer tube 50 by which the pots are passed to the sampling installation. The pneumatic drum 52 constitutes an isolating or insulating means positioned above the rotary plug 20 in the axis of the latter. A flexible tube 54 connects the drum 52 to the upper end of a vertical transfer duct 60, which traverses the rotary plug 20. The flexible nature of the tube 54 makes it possible to take account of the displacements of the pot transfer duct 60 traversing the rotary plug 20 with respect to the pneumatic drum 52.

As indicated hereinbefore, the pneumatic drum 52 constitutes an insulating means permitting, when it occupies a first insulating position, the insulation of the transfer tube 50 and the flexible tube 54 with respect to one another. The pneumatic drum 52 can also occupy a transfer or passage position, in which the transfer tube 50 and the flexible tube 54 are linked with one another.

For this purpose, the pneumatic drum or insulating means corresponding thereto can be produced in different ways. For example, it can be a drum having a gate valve in which is formed a passage not aligned with the transfer tube 50 when the drum is in the insulating position, said passage linking the transfer tube 50 and the flexible tube 54 in the passage position of the drum.

As is very diagrammatically illustrated in FIG. 1, the pneumatic drum 52, the pump 46 and the auxiliary installations which will be described hereinafter are advantageously installed on a horizontal plate 56 placed above the rotary plug 20 and connected to the slab 12, in the vicinity of said plug, by a support beam 58.

As is more specifically illustrated by FIG. 2, the duct 60 for transferring the pots 44 and to which is connected the lower end of the flexible tube 54, traverses in a vertical direction a cylindrical element 62 of the slab 12. More specifically, said cylindrical element 62 is placed in a circular opening 64 formed in a rotary plug 20, so as to be able to move vertically between two end positions without breaking the confinement.

It should be noted that the axis of the cylindrical element 62 and the axis of the transfer duct are positioned at the same distance from the vertical axis of the rotary plug 20 as the confinement pin 42. Consequently the rotation of the rotary plug 20 has the effect of making the axes of the cylindrical element 62 and the transfer duct 60 describe a circular arc located equidistantly of the circular arcs over which are distributed the needles 40. Moreover, said distance separating the circular arc described by the axis of the cylindrical element 62 from the arcs on which are located the needles 40 is equal to the distance separating the axis of the vertical transfer duct 60 from the axis of the cylindrical element 62.

The two end positions which can be occupied by the element 62 respectively corresponding to an upper waiting position, in which the lower face of the cylindrical element is flush with the lower face of the rotary plug 20 and a lower sampling position, in particular making it possible to engage the plug of a pot on one of the needles 40 for carrying out sampling, as will be shown hereinafter.

The displacement of the cylindrical element 62 between its two positions is controlled by a direct current motor 66 shown in FIG. 1. The body of said motor 66 is mounted on a support 68 connected by vertical posts 70 to a flange projecting upwards over the rotary plug 20 around the cylindrical element 62.

A not shown differential, linear displacement transducer controls the position of the cylindrical element 62. The lower position of said element is also detected by a not shown inductive sensor.

The cylindrical element 62 normally occupies its upper waiting position and its descent is only possible when the rotary plug 20 is locked by the bolt 33 in a given angular position.

As is more particularly illustrated by FIGS. 2 and 3, the cylindrical element 62 supports in rotary manner a pot-holding drum 72 positioned below said element and whose rotation axis coincides with the vertical axis of the latter.

The pot-holding drum 72 mainly comprises a horizontal disk 74 located immediately below the cylindrical element, as well as a pot receiving nacelle, pod or basket 76, which generally has the shape of a tube traversing the disk 74 and which projects from the bottom of the latter. The internal diameter of the nacelle 76 is identical to that of the transfer duct 60 and has at its lower end a shoulder 78 on which can bear a pot 44, when the nacelle 76 is located in the alignment of the transfer duct 60, as illustrated in FIG. 3. The length of the nacelle 76 is such that when a pot 44 bears against the shoulder 78, the upper end of the pot is located slightly below the upper plane of the disk 74, which permits the rotation of the drum 72.

The rotary drum 72 also has a hollow control shaft 80, which traverses along its axis the cylindrical element 62, so that the latter supports the drum in rotation about said axis.

The control shaft 80 also ensures the rotation control of the drum by a direct current motor 81 fitted above the cylindrical element 62 and whose vertical output shaft 82 rotates a pinion 84, which meshes on a toothed wheel 86 formed at the upper end of the control shaft 80.

During its rotation, the drum 72 can occupy three preselected positions at 120° from one another.

Figure 3:
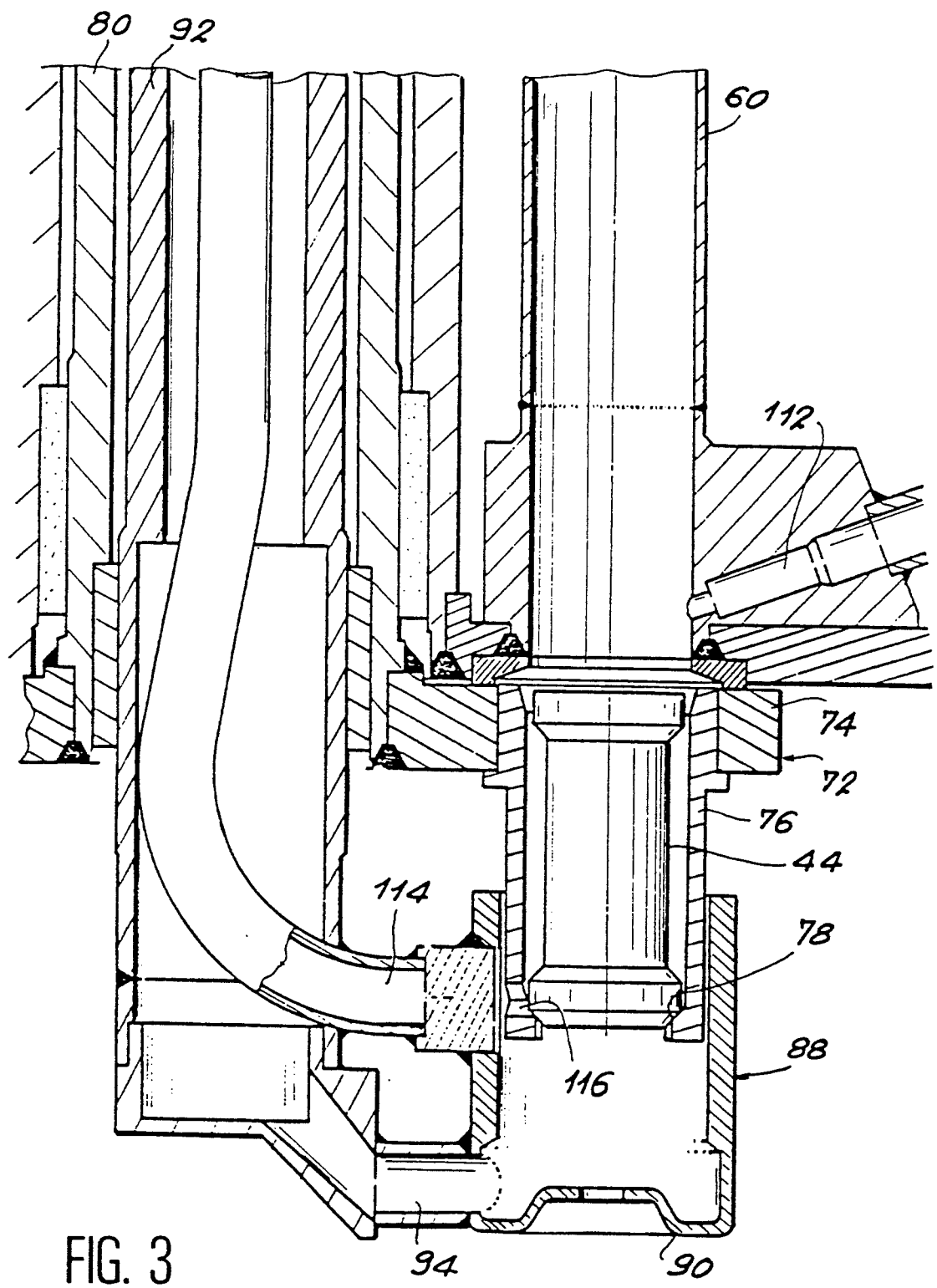
FIG. 3 A vertical sectional view showing the rotary drum carrying the nacelle for receiving the pot, as well as the anti-tear out member associated with said nacelle.

A first position $P_0$ (FIG. 5), particularly illustrated in FIGS. 2 and 3, corresponds to the alignment of the nacelle 76 with the transfer duct 60. This position, which corresponds to the arrival or departure of a pot 44, also permits by a rotation of the rotary plug 20 and then a descent of the cylindrical element 62 the bringing of the lower end of the nacelle 76 so as to engage on the confinement pin 42, to ensure a confinement between the closed volume 18 defined by the vessel 14 and the transfer duct 60.

The two other preselected positions $P_{120}$ and $P_{240}$ (FIG. 5) of the drum 72 make it possible to bring the axis of the nacelle 76 above one or other of the circular arcs over which are distributed the needles 40. Therefore these positions make it possible to bring a pot 44 located in the nacelle 76 above any random one of the needles 40, by a rotation of the rotary plug 20, so as to carry out the desired sampling operations.

The position of the drum 72 is continuously given by an angular measurement obtained with the aid of a not shown linear displacement transducer operated by a cam integral with the drum.

The sampling installation according to the invention also comprises an anti-tear off member 88, shown in detail in FIG. 3 and whose function is to maintain the body of the needle 40 fitted in the receptacle 39 of the sampling container 38, when a pot 44 has been engaged on the needle for carrying out a sampling operation is moved upwards in order to completely free the pot from the corresponding needle.

This anti-tear out member 88 is shaped like a sleeve surrounding that part of the nacelle 76 which projects below the plate 74. This sleeve is closed at its base by a plate 90, which is centrally perforated in order to permit the passage of the needles 40 and also in such a way as to be fittable onto the confinement pin 42.

The anti-tear off member 88 is fitted on the nacelle 76, so as to be able to move vertically between a top position, in which the plate 90 is flush with the lower end of the nacelle, and a bottom position, illustrated in FIG. 3, in which said plate 90 is at a given distance below the lower end of the nacelle.

The supporting of the anti-tear off member 88, permitting its displacement between these two positions, is ensured by a rigid tube 92 traversing the cylindrical element 62 within the hollow control shaft 80 and whose lower end carries the member 88 via a connecting tube 94 issuing into the anti-tear off member 88 just above the plate 90.

Elastic means such as a spring 96 (FIG. 2) are interposed between the upper end of the hollow control shaft 80 and the upper end of the rigid tube 92, above the cylindrical element 62, so as to normally maintain the anti-tear off member 88 in its bottom position with respect to the nacelle 76.

Besides their supporting function with respect to the anti-tear off member 88, the rigid tube 92 and the connecting tube 94 constitute a closed pneumatic circuit, connected by the upper end of the rigid tube 92 to an air supply pipe 98, which can be seen in FIGS. 1 and 6. This air supply pipe 98 is linked by a first electrovalve 100 to ventilation means of the vessel 14 and by a second electrovalve 102 with compressed air supply means serving, as will be shown hereinafter, to raise up to the pneumatic drum 52 a pot in which sampling has taken place.

Under normal operating conditions of the installation the electrovalve 100 is open for ventilating the vessel 14. However, the electrovalve 102 is closed. The air supply pipe 98 and the rigid tube 92 thus constitute, when they are connected by the electrovalve 102 to compressed air supply means, part of the means for the pneumatic transfer of the pots through the slab 12.

These pneumatic pot transfer means also incorporate means for aiding the descent of the pots into the nacelle 76, which normally takes place by gravity. These means comprise a second air supply pipe 104 (FIG. 6), which is linked with the compressed air supply means through a third electrovalve 106. This air supply pipe 104 issues into the transfer tube 50 just above the pneumatic drum 52. After opening the electrovalve 106 and when the pneumatic drum 52 links the transfer tube 50 with the flexible tube 54, said means make it possible to pneumatically assist the descent of each pot from the drum 52 into the nacelle 76, which is then aligned with the transfer duct 60.

The sampling installation according to the invention also has a certain number of detectors making it possible to know at all times the precise position occupied by a pot within the installation.

These detectors in particular include a detector 108 (FIG. 6) of the passage of a pot into the transfer tube 50 detecting the arrival of a pot level with the pneumatic drum 52. This detector 108, as well as a second detector 110 placed in the flexible tube 54 immediately below the pneumatic drum 52, can in particular be constituted by optical fibre detectors.

As is more specifically illustrated by FIG. 3, a third optical fibre detector 112 is installed in the cylindrical element 62, in the bottom of the transfer duct 60, in order to detect the passage of a pot 44 and the absence of a pot in the cylindrical element when a sampling operation is performed. This detector 112 ensures that a pot 44 is not sheared by a rotation of the drum 72.

Finally, a fourth optical fibre detector 114, whose optical fibre travels within the tube 92, is placed on the anti-tear off member 88 and faces a hole 116 formed in the nacelle 76 level with the shoulder 78, when the member 88 is in the bottom position relative to the nacelle and as illustrated in FIG. 3. This detector 112 ensures the presence of a pot 44 in the nacelle 76 before sampling takes place.

The sampling installation for fluids described hereinbefore with reference to FIGS. 1 to 6 functions in the following way.

When no sampling operation is taking place, the pneumatic drum 52 is in its isolating or insulating position and the vessel 14 is ventilated by air injected through the electrovalve 100 by the air supply pipe 98 and the rigid tube 92. Moreover, the cylindrical element 62 is in the upper position, the nacelle 76 aligned with the transfer duct 60 and the rotary plug 20 indexed in its angular position for which the duct 60 and nacelle 76 are positioned above the confinement pin 42.

When a sampling operation has to take place, a pot under vacuum is sent from the not shown distribution station to the pneumatic drum 52 by the transfer tube 50 under the action of the pump 46. When it arrives above the drum 52, the pot is detected by the detector 108. The suction station materialized by the pump 46 is then stopped.

The electrovalve ensuring the ventilation of the vessel 14 is then closed. The pneumatic drum 52 is then actuated in order to link the transfer tube 50 and the flexible tube 54. Simultaneously, the electrovalve 106 is opened in order to ensure an entrance of pressurized air above the vacuum pot previously stopped by the pneumatic drum 52.

Figure 7A:
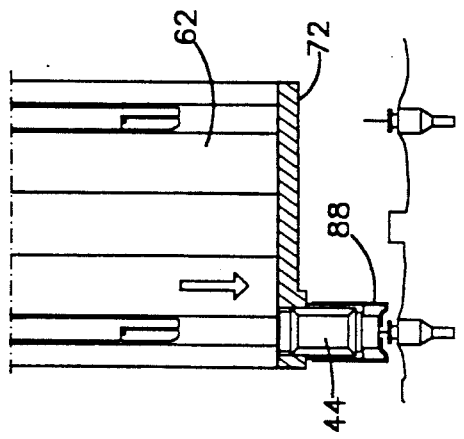
FIGS. 7A to 7F Vertical sectional views illustrating different operating phases of the sampling installation according to the invention, when said installation is installed for carrying out a sampling operation.

The joint action of the compressed air admitted by the electrovalve 106, gravity and the vacuum in the vessel 14 have the effect of lowering the pot into the flexible tube 54 and then in the transfer duct 60 to the interior of the nacelle 76, as illustrated in FIG. 7A. The passage of the pot is successively detected by the transducer 110, the transducer 112 and then the transducer 114. The electrovalve 106 is then closed again and the pneumatic drum 52 brought into its insulating position.

In accordance with the circular arc on which is located the needle 40 corresponding to the sampling to take place, the drum 72 then turns by 120° or 240°, so that it passes from position $P_0$ to position $P_{120}$ or $P_{240}$, as is diagrammatically illustrated in FIG. 5.

Figure 7C:
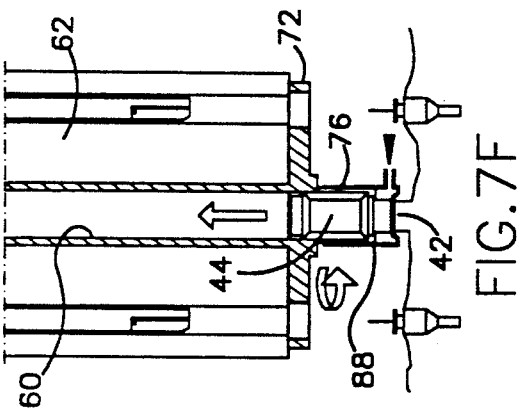
Figure 7B:
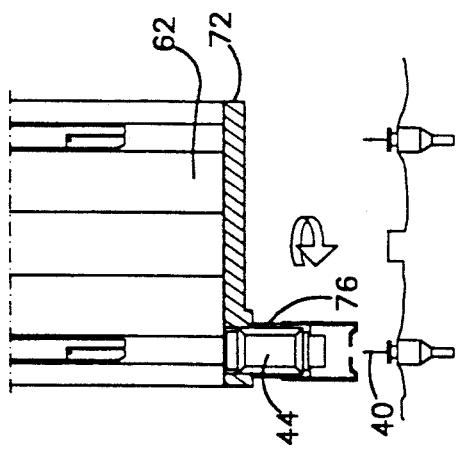

In order to bring the nacelle 76 carrying the vacuum pot 44 above the needle 40 on which a sampling is to take place, the rotary plug 20 is also turned until the axis of the nacelle 76 is positioned vertically with respect to said needle. The pot 44 contained in the nacelle 76 thus passes into a position of selecting the needle in question, as illustrated in FIG. 7B.

The cylindrical element 62 then moves downwards carrying with it the drum 72 and the anti-tear out member 88. After the latter has covered the body of the corresponding needle 40, the descent of the cylindrical element 62 and the drum 72 continues, so that the needle 40 perforates the rubber plug sealing the lower end of the pot 44. It should be noted that the latter is then maintained in opposition to any upward displacement by its bearing against the lower face of the cylindrical element 62, because the nacelle 76 is then angularly displaced with respect to the transfer duct 60. Under these conditions, illustrated in FIG. 7C, sampling takes place automatically under the effect of the suction created by the vacuum present within the pot 44.

Figure 7E:
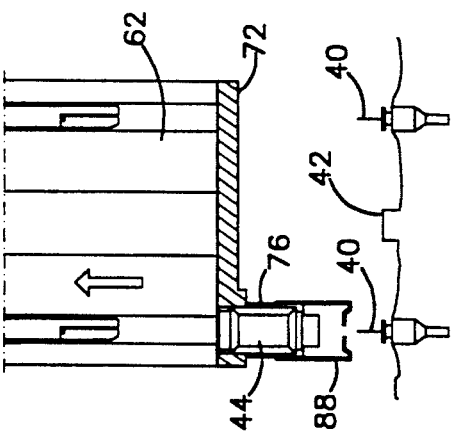
Figure 7D:
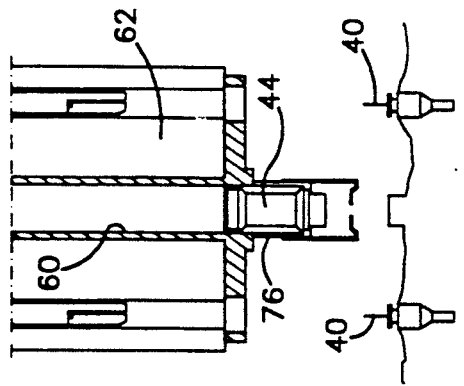

When the time necessary for sampling has elapsed, the cylindrical element 62 rises, carrying with it the nacelle 76 containing the pot 44 containing the sample. At the start of this movement and whilst the needle 40 remains engaged in the plug of the pot 44, the anti-tear off member 88 remains engaged against the body of the needle 40 under the action of the spring 76 (FIG. 2). This characteristic, illustrated in FIG. 7D, avoids the needle 40 being torn out of its sampling container under the effect of the raising of the pot. Then and as illustrated in FIG. 7E, the anti-tear off member 88 rises with the cylindrical element 62 and the nacelle 76 containing the pot 44.

Sampling is then at an end and the pot can be dispatched to an analysis laboratory. For this purpose, it is discharged from the installation by the same way by which it entered. For this purpose the drum 72 is brought by a further rotation from its $P_{120}$ or $P_{240}$ position into its initial $P_0$ position and a further rotation of the rotary plug 20 brings the transfer duct 60 and the nacelle 76 containing the pot into a vertical orientation with respect to the confinement pin 42 and which determines, as has been shown, the position in which the evacuation of the pots takes place.

Figure 7F:
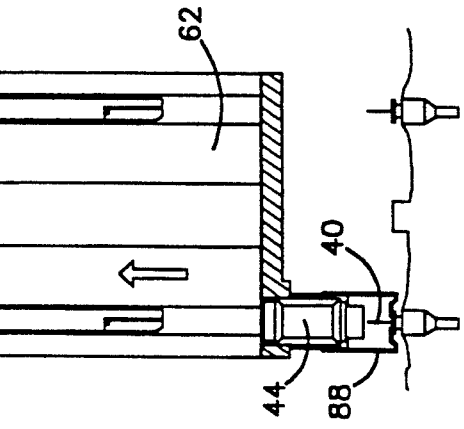

When this position is reached, the cylindrical element 62 is lowered so that the hole formed in the plate 90 of the anti-tear out member 88 is sealed by the confinement pin 42. The internal volume 18 of the vessel 14 is then isolated from the transfer duct 60, so that the pneumatic drum 52 can be brought into its passage position. The electrovalve 102 is then opened, which has the effect of injecting compressed air below the pot contained in the nacelle 76 by the pipe 98, the rigid tube 92 and the connecting tube 94, as illustrated in FIG. 7F. This compressed air controls the raising of the pot 44 containing the sampled material into the transfer duct 60, into the flexible tube 54 and then into the transfer tube 50, which is then linked with the tube 54 through the pneumatic drum 52. The pot is then moved up to the appropriate analysis laboratory by suction with the aid of a suction installation associated with said laboratory and comparable to that illustrated by pump 46 in FIG. 1.

When the pot containing the sample enters the transfer tube 50, the pneumatic drum 52 returns to its isolation position, the electrovalve 102 closes again and the other elements of the installation return to their previously described initial state.

The fluid sampling installation, whose structure and operation have been described hereinbefore is advantageously equipped with means making it possible to dismantle the needles 40 which have become blocked or damaged and replace them by new needles.

As is more particularly illustrated by FIGS. 7A and 7B, these means essentially comprise two gripping tools, which are vertically installed in the cylindrical element 62 at locations angularly spaced by respectively 120° and 240° relative to the axis of the transfer duct 60, about the axis of the cylindrical element 62 and at the same distance from the axis of the element 62 as the axis of the transfer duct 60.

Each of these gripping tools 118 is located in a cylindrical cavity 120, which has a vertical axis and which is formed within a tool-holder sleeve 122. It should be noted that the diameter of each of the cavities 120 is smaller than the diameter of the transfer duct 60, so that the lower end of each of the tool-holder sleeves 122 serves as an abutment for the pot 44 placed in the nacelle during the previously described sampling operation and during which the pots are located below one or other of the cavities 120.

Each of the gripping tools 118 has a cylindrical body 124, which is vertically movable in the corresponding cavity 120. The cylindrical body 124 supports a clip or clamp 126 at its lower end. Said clamp 126 comprises a fixed jaw 128 integral with the body 124 and a mobile jaw 130 articulated to the fixed jaw 128 by a spindle 132 orthogonal to the longitudinal axis of the cavity 120.

The pivoting control of the mobile clamp jaw 130 is ensured by a rod 132, which slides along the axis of the cavity 120 within the cylindrical body 124 and whose lower end is connected to the mobile jaw 130 by an articulated link 134. The downward displacement of the rod 132 corresponding to the closing of the clamp 126 is ensured by a not shown electromagnet interposed between the said rod and the cylindrical body 124.

The displacement of the gripping tool 118 within the cavity 120 is controlled by a not shown direct current motor, which is checked by a not shown linear displacement transducer.

The characteristics of the two identical gripping tools are such as to permit the gripping by each of them of a needle 40 (FIGS. 8A and 8B) or the plug of a container, whose shape is generally identical to that of the pots 44 and which is used for transporting the new and used needles 44. To this end, the ends of the jaws 128 and 130 are in the form of hooks, which can be placed on the collars 135 formed on the body of the needles 40 and on the plug of the needle transporting containers.

A single, not shown linear displacement transducer controls the stopping of the gripping tool 118 during its downward displacement prior to the engagement of a plug or needle.

As illustrated by FIGS. 7A and 7B, the disk 74 of the drum 72 has two passages 140 aligned with the cavities 120 when the nacelle 76 is aligned with the transfer duct 60 and whose diameter is slightly larger than that of the cavities.

As a result of the two gripping tools 118 installed in the cylindrical element 62 of the rotary plug, it is possible by two successive operations integrally controlled in a remote manner, to dismantle or remove a used needle and then replace it by a new needle, as will be described relative to FIGS. 9A to 9F and then 10A to 10F. In this description, in order to distinguish them despite their identity, the references of the two gripping tools and the corresponding cavities are followed by the letters a and b.

Firstly and as is diagrammatically illustrated in FIG. 9A, an empty container 136 able to contain a needle is introduced into the nacelle 76 in an identical manner to the introduction of a pot 44 into said same nacelle and as described hereinbefore.

A 120° or 240° rotation of the drum 72 then makes it possible to bring the nacelle 76 below the gripping tool 118a, whose axis is aligned with the circular arc not having a needle 40a to be replaced. A rotation of the rotary plug 20 also brings the axis of the other tool 118b into a vertical position with respect to the needle 40a to be replaced. The tool 118a is then lowered and its clamp actuated, so as to grasp the plug 138 of the container 136 and then retract said plug into the cavity 120a containing the gripping tool 118a. This stage is diagrammatically illustrated by FIG. 9B.

As a result of a further rotation of the drum 72, the nacelle 76 is brought into its initial position of alignment with the transfer duct 60. The effect of this rotation is to bring the two passages 140 formed in the plate 74 of the drum 72 below each of the cavities 120a, 120b. The gripping tool 118b is then lowered and its clamp 126 actuated so as to grasp the needle 40a, followed by retraction into the corresponding cavity 120b. These operations are diagrammatically illustrated in FIG. 9C.

As is shown in FIG. 9D, a further rotation of the drum 72 then brings the nacelle 76 housing the container 156 free from its plug below the gripping tool 118b carrying the needle 40a to be replaced. A further lowering of the tool 118b and then an operation of its clamp makes it possible to place the needle 40a to be replaced in the container 136.

Following the raising of the gripping tool 118b, the drum 72 is rotated again, as illustrated in FIG. 9E and this has the effect of bringing the nacelle 76 housing the container 136 containing the needle 40a into a vertical position with respect to the gripping tool 118a, which still carries the plug of the container. The latter is then sealed by lowering the gripping tool 118a and thus releasing the plug by an actuation of its clamp.

The tool 118a is in turn retracted into the cylindrical element 62 and a further combined rotation of the drum 72 and the rotary plug 20 makes it possible to align the nacelle 76, the transfer duct 60 and the confinement pin 42. Under these conditions, the container 136 containing the used needle 40a can be discharged, in the same way as a pot 44, by the lowering of the cylindrical element 62 having the effect of isolating the transfer duct 60 from the internal volume of the vessel 14 with the aid of the confinement pin 42 and then by an injection of compressed air below the nacelle 76 controlled by an opening of the electrovalve 102 (FIG. 9F).

The putting into place of a new needle 40b can then be envisaged, in the manner diagrammatically illustrated in FIGS. 10A to 10F. Firstly, a container 136 transporting a new needle 40 is introduced into the nacelle 76 in the manner described hereinbefore for the pots 44. This first stage is illustrated in FIG. 10A.

Then and as illustrated in FIG. 10B, the drum 72 is rotated in order to bring the nacelle 76 in front of the gripping tool 118a, which is not located on the circular arc having the receptacle 39 of the needle-free sampling head. The gripping tool 118a is then operated so that it grasps the plug 138 of the container 136 and retracts it into the corresponding cavity 120a.

A further rotation of the drum 72, illustrated in FIG. 10C, makes it possible to bring the nacelle 76 containing the open container 136 and which contains the new needle 40b into a vertical position with respect to the second gripping tool 118b. The latter is then operated so as to grasp the new needle 40b and retract it into the corresponding cavity 120b through the passage 140.

As illustrated in FIG. 10D, the drum 72 is then rotated again so as to have the effect of bringing the nacelle 76 into a vertical position with respect to the gripping tool 118a carrying the plug 138. The latter can thus be put back into place on the container 136, which is then empty.

This empty container 136 is then discharged following a further rotation of the drum 72 bringing the nacelle 76 containing the empty container and sealed by its plug 138 into the extension of the transfer duct 60, which is then positioned vertically of the confinement pin 42. The discharge of the container is brought about in the same way as hereinbefore by lowering the cylindrical element 62 so as to isolate the internal volume of the vessel 14 from the transfer duct 60 with the aid of the confinement pin 42, as illustrated in FIG. 10E, using compressed air injected below the nacelle 76 by tubes 92, 94, opening the electrovalve 102.

The cylindrical element 62 is then raised and the gripping tool 118b carrying the new needle 40b is brought vertical of the receptacle 39 of the needle-free gripping head by a rotation of the rotary plug 20. The new needle 40b can then be introduced into the receptacle by the combined descent of the cylindrical element 62 and the needle-carrying gripping tool 118b. This stage is diagrammatically illustrated in FIG. 10F. When completed, the different members of the installation according to the invention are returned to their previously described initial state.

FIG. 10B also illustrates in greater detail the introduction of the new needle 40b into the receptacle 39 of the corresponding sampling head with the aid of the gripping tool 118.

Obviously, the invention is not limited to the embodiment described in exemplified manner hereinbefore and covers all variants thereof. Thus, in the particular case where the vessel 14 only contains one or two sampling heads, it is possible to eliminate the rotary plug 20.

I claim:

1. Installation for taking fluid samples in a confined area located below a protective slab, said installation comprising a sampling vessel located below the slab, at least one sampling needle traversing a bottom of the slab and remote handling means for transferring individually sampling pots into and out of the vessel through the slab and for engaging each pot individually on a said at least one sampling needle in order to perform a sampling operation, wherein said remote handling means comprise:

a pot transfer duct, traversing a slab element, which is vertically mobile between an upper waiting position and a lower sampling position;

a drum rotatably mounted beneath said slab element, about an axis displaced with respect to that of the duct, and having a pot reception nacelle which can be brought, by the rotation of the drum, into an angular pot reception and evacuation position, in which the nacelle is placed below the duct, and into at least one-angular sampling position, in which the nacelle can be brought above the said at least one sampling needle; and means for the pneumatic transfer of the pots upwards and downwards in said duct.

2. Installation according to claim 1, wherein the remote handling means comprise several sampling needles arranged along at least one circular arc having an axis displaced with respect to the axis of the drum and a rotary plug whose axis corresponds with the axis of the circular arc and forming above the vessel a part of the slab and in which is housed said slab element, so that in said angular sampling position of the nacelle, the latter can be brought above each of the needles by a rotation of the rotary plug.

3. Installation according to claim 1, wherein the remote handling means comprise rotation control means for the drum and installed on said slab element so as to act on a control shaft traversing the slab element in accordance with an axis of said slab element and integral with the drum at a lower end thereof.

4. Installation according to claim 3, wherein the pneumatic transfer means for the pots comprise an air supply pipe, which travels in said control shaft and issues below the nacelle.

5. Installation according to claim 4, wherein the air supply pipe is linked with ventilation means for the vessel through first means forming a valve and with compressed air supply means through second means forming a valve.

6. Installation according to claim 4, wherein there are a plurality of sampling needles and each sampling needle is fitted into a receptacle provided in a bottom of the vessel, so that the remote handling means comprise an anti-pull out member fitted on the nacelle so as to be displaceable thereon between an upper position in which said member is flush with a lower end of the nacelle and a lower position in which said member is spaced from the lower end of the nacelle by a distance substantially equal to the length of a part of each needle projecting above the receptacle.

7. Installation according to claim 6, wherein the anti-pull out member is moved towards its lower position by elastic means.

8. Installation according to claim 6, wherein the air supply pipe incorporates a rigid tube, slidingly housed within the control shaft and which carries the anti-pull out member at a lower end thereof.

9. Installation according to claim 6, wherein said slab element has two cavities, whereof at least one can be brought above a needle and under each of which can be brought the nacelle as a result of the rotation of the drum, a gripping tool being slidingly housed in each of the cavities and which is able to grasp a pot plug and a needle.

10. Installation according to claim 9, wherein each of the gripping tools incorporates a clamp mounted at a lower end of a body sliding in the cavity, and clamp having at least one pivoting jaw, whose pivoting is controlled by a rod able to slide in the body.

11. Installation according to claim 1, wherein a bottom of the vessel has a confinement member able to seal a needle passage orifice formed in a lower end of the nacelle, when the slab element is in the lower position and when the nacelle is placed below the pot transfer duct.

12. Installation according to claim 1, wherein the remote handling means comprise a detector of the presence of a pot in the nacelle.

13. Installation according to claim 1, wherein the remote handling means also incorporate isolating means placed above the slab and connected to the pot transfer duct by a flexible tube, said isolating means being able to occupy an isolating position, in which the flexible tube is isolated from a transfer tube placed above the isolating means, and a passage position in which the flexible tube and the transfer tube are interlinked.

14. Installation according to claim 13, wherein the remote handling means comprise a detector of the passage of a pot in the transfer tube above the isolating means.

15. Installation according to claim 13, wherein the pneumatic pot transfer means have an air supply pipe, which is linked with a compressed air supply means through means forming a valve and which issues into the transfer tube immediately above the isolating means.

* * * * *